(12) United States Patent
Roe et al.

(10) Patent No.: US 6,623,465 B1
(45) Date of Patent: Sep. 23, 2003

(54) ABSORBENT ARTICLE WITH WATER-ACTIVATABLE TOPICAL ADHESIVES

(75) Inventors: Donald C. Roe, West Chester, OH (US); Mark J. Kline, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/504,985

(22) Filed: Feb. 15, 2000

(51) Int. Cl.[7] ................................................ A61F 13/15
(52) U.S. Cl. ............................ 604/385.03; 604/385.28; 604/389
(58) Field of Search ................................ 604/367, 375, 604/383, 385.01, 385.23, 385.24, 385.03, 386, 387, 389, 385.28, 332, 307, 364

(56) References Cited

U.S. PATENT DOCUMENTS

| 3,575,173 A |   | 4/1971  | Loyer |
|---|---|---|---|
| 3,612,053 A | * | 10/1971 | Pratt ........................... 128/283 |
| 3,777,759 A |   | 12/1973 | Oehmke et al. ............. 128/287 |
| 4,199,646 A |   | 4/1980  | Hori et al. .................... 428/344 |
| 4,699,146 A |   | 10/1987 | Sieverding ................... 128/640 |
| 5,066,711 A |   | 11/1991 | Colon et al. |
| 5,071,415 A | * | 12/1991 | Takemoto .................... 604/389 |
| 5,156,911 A |   | 10/1992 | Stewart ........................ 428/355 |
| 5,348,546 A | * | 9/1994  | Norton ......................... 604/333 |
| 5,387,450 A |   | 2/1995  | Stewart .......................... 428/40 |
| 5,589,246 A |   | 12/1996 | Calhoun et al. ............. 428/120 |
| 5,613,942 A |   | 3/1997  | Lucast et al. |
| 5,633,010 A |   | 5/1997  | Chen ............................ 424/448 |
| 5,648,167 A |   | 7/1997  | Peck ............................. 428/355 |
| 5,681,306 A |   | 10/1997 | Goulait et al. |
| 5,782,787 A |   | 7/1998  | Webster ......................... 602/46 |
| 5,876,745 A |   | 3/1999  | Muraoka et al. ............ 424/448 |
| 5,889,118 A |   | 3/1999  | Delgado et al. ............. 525/228 |
| 6,095,996 A | * | 8/2000  | Steer et al. .................... 602/52 |
| 6,168,583 B1 | * | 1/2001 | Tanji et al. ............. 604/385.14 |

FOREIGN PATENT DOCUMENTS

| EP |     0 850 625 A1 | 7/1998  |                |
|----|------------------|---------|----------------|
| WO | WO 95/05934      | 3/1995  | ......... B29C/65/50 |
| WO | WO 98/29517      | 7/1998  | ......... C09J/129/10 |
| WO | WO 98/58035      | 12/1998 | ......... C09J/153/02 |
| WO | WO 99/63018      | 12/1999 | ............ C09J/7/02 |
| WO | WO 00/00123 A1   | 1/2000  |                |
| WO | WO 00/32142 A1   | 6/2000  |                |
| WO | WO 00/38748      | 7/2000  | ......... A61L/15/58 |

* cited by examiner

Primary Examiner—Weilun Lo
Assistant Examiner—Jamisue A Webb
(74) Attorney, Agent, or Firm—David M. Weirich; Eileen L. Hughett; Edward J. Milbrada

(57) ABSTRACT

An absorbent article that includes a topsheet, a backsheet that is at least partially joined to the topsheet and an absorbent core that lies between the topsheet and the backsheet are described. A water activatable adhesive that, when activated, can adhere to a wearer's skin is also deposited on at least part of the absorbent article is also described.

8 Claims, 9 Drawing Sheets

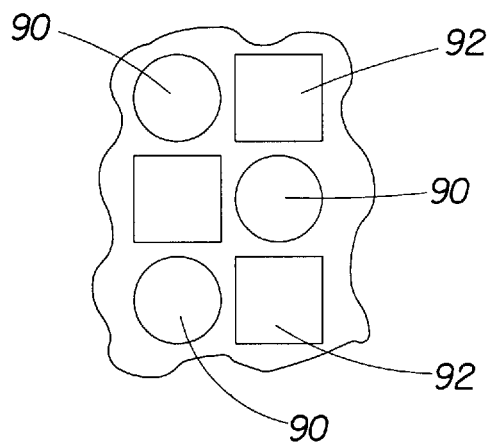
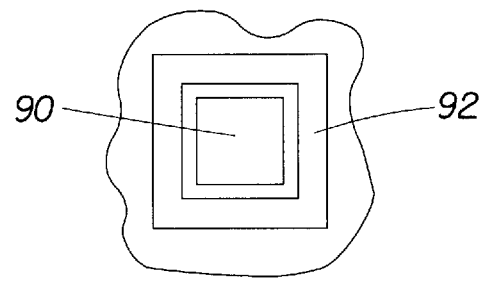
Fig. 9A          Fig. 9B
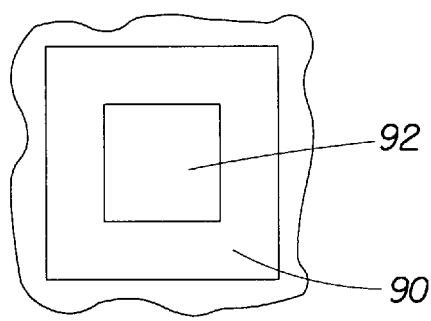
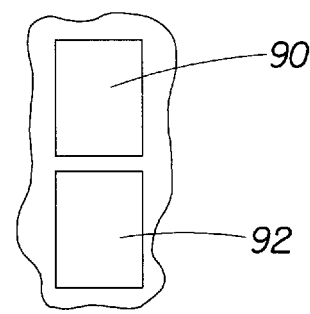
Fig. 9C          Fig. 9D
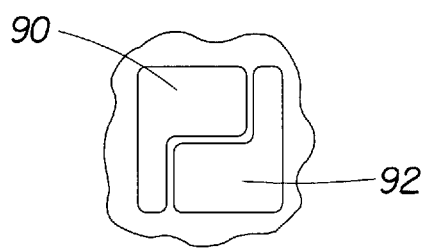
Fig. 9E

ABSORBENT ARTICLE WITH WATER-ACTIVATABLE TOPICAL ADHESIVES

FIELD OF THE INVENTION

This invention is directed to hygienic absorbent articles, such as diapers, adult incontinence articles, feminine protection articles and the like. More particularly, the invention relates to absorbent articles including water-activatable topical adhesives.

BACKGROUND OF THE INVENTION

Absorbent articles are well known in the art. These articles typically have an absorbent core, which is held or positioned against the body of the wearer during use by a fastening system, such that the bodily exudates are caught by the article. Typical absorbent articles include a topsheet facing the wearer which permits fluid exudates to pass through and a backsheet which prevents the exudates from escaping from the absorbent article.

Many advancements have been made in the art since the introduction of the disposable absorbent article. However, problems still exist relating to isolation of bodily waste, such as fecal material, and application of the article. Attempts have been made to isolate fecal waste by employing pockets, topsheets with receiving apertures, spacing elements, barrier cuffs, and other physical means. These generally have the deficiency of difficulty maintaining coordination with the wearer's body, especially the waste outlet points. Attempts have also been made to improve the application of the article to the wearer by the use of adhesive tapes and mechanical fastening systems such as Velcro®. However, the articles are still difficult to apply to mobile wearers using only two hands.

In an effort to overcome the deficiencies of the prior art, topical adhesives such as hydrocolloid, silicone, and hydrogel adhesives have been incorporated into disposable articles as a means of better positioning the article or maintaining body contact. However, these attempts fail to provide an adequately convenient means of using the product because they require release paper to prevent accidental contamination of the adhesive during manufacture, storage, and preparation. Additionally, such embodiments may result in inadvertent sticking of the article to the caregiver's hands and/or the wearer's clothing, legs, etc. (e.g., regions of the body outside the intended attachment area).

Thus, it would be desirable to provide absorbent articles with improved fit and sealing which can be sustained during use. It would also be desirable to provide an article which maintains coordination with a specific area of the wearer's anatomy. Further, it would be advantageous to provide an article with a water-activatable topical or body adhesive which helps maintain the article in the desired configuration without irritating or harming the wearer's skin. Even further, it would be advantageous to provide an article having a water-activatable topical adhesive which is activatable during the course of applying or wearing the article.

SUMMARY OF THE INVENTION

The present invention solves the problems of the prior art by providing an absorbent article comprising a topsheet, a backsheet joined with at least a portion of the topsheet, an absorbent core disposed between at least a portion of the topsheet and the backsheet and a water-activatable adhesive disposed on at least a portion of the article for adhering of the absorbent article to the wearer during use. In a preferred embodiment, the water-activatable adhesive is substantially anhydrous prior to activation.

BRIEF DESCRIPTION OF THE DRAWINGS

FIGS. 9A–9E are plan views of alternative embodiments of fastening systems suitable for use with the present invention.

DETAILED DESCRIPTION OF THE INVENTION

As used herein, the term "absorbent article" refers to devices which absorb and contain body exudates, and more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner). (As used herein, the term "disposed" is used to mean that an element(s) of the diaper is formed (joined and positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons about the lower torso. The present invention is also applicable to other absorbent articles such as incontinence briefs, incontinence undergarments, absorbent inserts, diaper holders and liners, feminine hygiene garments, wipes, mops, bandages and the like.

Figure 1:
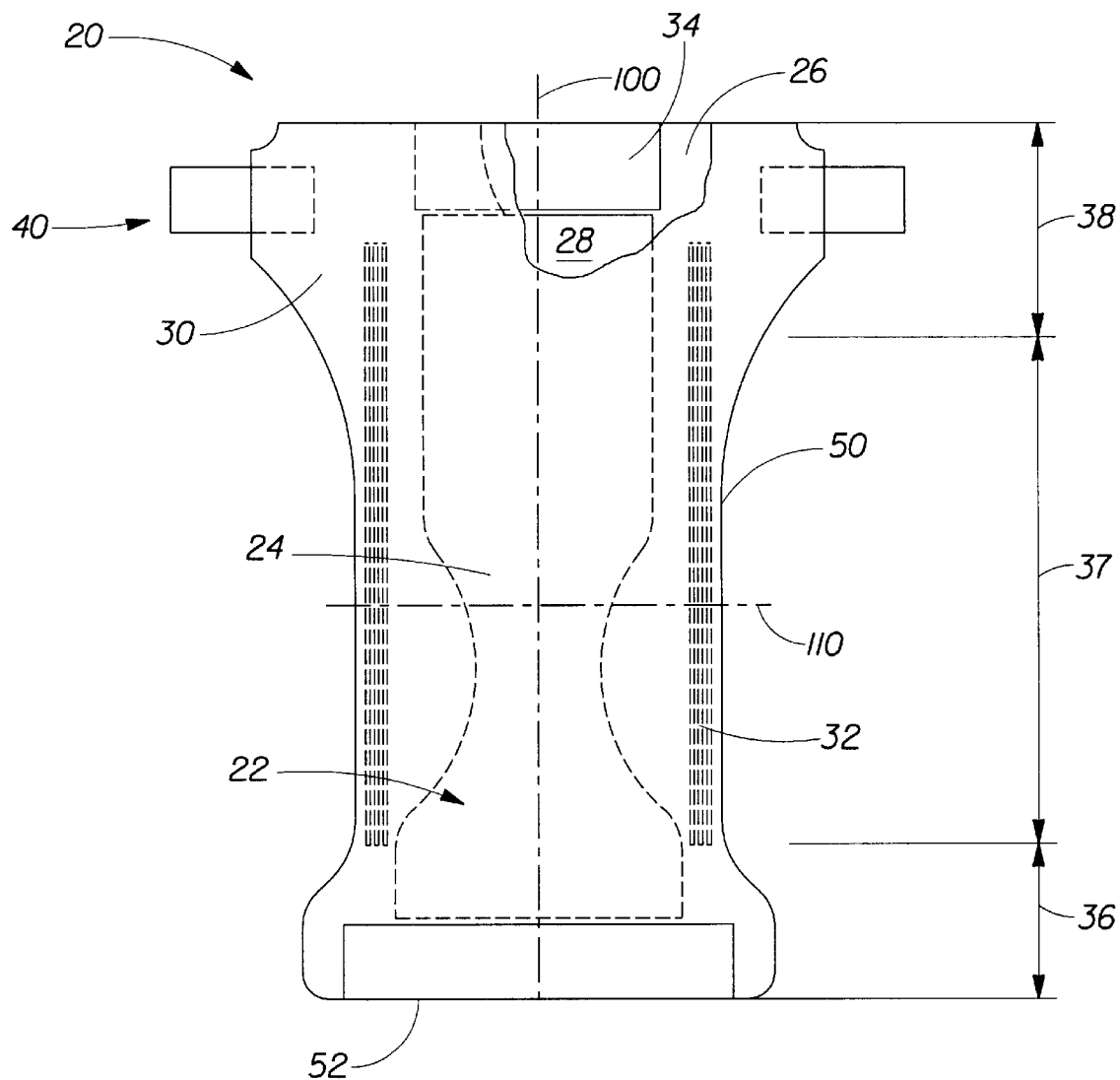
FIG. 1 is a plan view of a disposable diaper embodiment of the present invention with portions cut away to reveal underlying structure.

FIG. 1 is a plan view of the diaper 20 of the present invention in a flat-out, state with portions of the structure being cut-away to more clearly show the construction of the diaper 20. The portion of the diaper 20 which faces the wearer is oriented towards the viewer. As shown in FIG. 1, the diaper 20 preferably comprises a liquid previous topsheet 24; a liquid impervious backsheet 26; an absorbent core 28, which is preferably positioned between at least a portion of the topsheet 24 and the backsheet 26; side panels 30; elasticized leg cuffs 32; an elastic waist feature 34; and a fastening system generally designated 40. Diaper 20 is shown in FIG. 1 to have a first waist region 36, a second waist region 38 opposed to the first waist region 36 and a crotch region 37 located between the first waist region and the second waist region. The periphery of the diaper 20 is defined by the outer edges of the diaper 20 in which the longitudinal edges 50 run generally parallel to the longitudinal centerline 100 of the diaper 20 and the end edges 52 run between the longitudinal edges 50 generally parallel to the lateral centerline 110 of the diaper 20.

The chassis 22 of the diaper 20 comprises the main body of the diaper 20. The chassis 22 comprises at least a portion of the absorbent core 28 and preferably an outer covering layer including the topsheet 24 and the backsheet 26. If the absorbent article comprises a separate holder and a liner, the chassis 22 generally comprises the holder and the liner. For unitary absorbent articles, the chassis 22 comprises the main structure of the diaper with other features added to form the composite diaper structure. While the topsheet 24, the backsheet 26, and the absorbent core 26 may be assembled in a variety of well known configurations, preferred diaper configurations are described generally in U.S. Pat. No. 3,860,003 entitled "Contractible Side Portions for Disposable Diaper" which issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" which issued to Roe et al. on Sep. 10, 1996; U.S. Pat. No. 5,569,234 entitled "Disposable Pull-On Pant" which issued to Buell et al. on Oct. 29, 1996; U.S. Pat. No. 5,580,411 entitled "Zero Scrap Method For Manufacturing Side Panels For Absorbent Articles" which issued to Nease et al. on Dec. 3, 1996; and U.S. patent application Ser. No. 08/915,471 entitled "Absorbent Article With Multi-Directional Extensible Side Panels" filed Aug. 20, 1997 in the name of Robles et al.; each of which is incorporated herein by reference.

The backsheet 26 is generally that portion of the diaper 20 positioned adjacent the garment facing surface of the absorbent core 28 which prevents the exudates absorbed and contained therein from soiling articles which may contact the diaper 20, such as bedsheets and undergarments. In preferred embodiments, the backsheet 26 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962 and X10964. Other suitable backsheet materials may include breathable materials which permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE and monolithic films and composites such as manufactured by Clopay Corporation, Cincinnati, Ohio under the name HYTREL blend P18-3097. Some breathable composite materials are described in greater detail in PCT Application No. WO 95/16746, published on Jun. 22, 1995 in the name of E.I. DuPont and U.S. Pat. No. 5,865,823 issued to Curro on Feb. 2, 1999. Other breathable backsheets including nonwoven webs and apertured formed films are described in U.S. Pat. No. 5,571,096 issued to Dobrin et al. on Nov. 5, 1996. Each of these references is hereby incorporated by reference herein.

The backsheet 26, or any portion thereof, may be elastically extensible in one or more directions. In one embodiment, the backsheet 26 may comprise a structural elasticlike film ("SELF") web. A structural elastic-like film web is an extensible material that exhibits an elastic-like behavior in the direction of elongation without the use of added elastic materials and is described in more detail in U.S. Pat. No. 5,518,801 entitled Web Materials Exhibiting Elastic-Like Behavior, which issued to Chappell, et, al. on May 21, 1996, which is incorporated herein by reference. In alternate embodiments, the backsheet 26 may comprise elastomeric films, foams, strands, or combinations of these or other suitable materials with nonwovens or synthetic films.

The backsheet 26 may be joined to the topsheet 24, the absorbent core 28 or any other element of the diaper 20 by any attachment means known in the art. For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986 entitled "Disposable Waste-Containment Garment", which issued to Minetola et al. on Mar. 4, 1986. Other suitable attachment means include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Adhesives which have been found to be satisfactory are manufactured by H.B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

The topsheet 24 is preferably positioned adjacent the body facing surface of the absorbent core 28 and may be partially or wholly joined thereto and/or to the backsheet 26 by any attachment means known in the art. Suitable attachment means are described above with respect to means for joining the backsheet 26 to other elements of the diaper 20. In one preferred embodiment of the present invention, the topsheet 24 and the backsheet 26 are joined directly to each other in some locations and are indirectly joined together in other locations by directly joining them to other elements of the diaper 20.

The topsheet 24 may comprise one or more apertures 80 to ease penetration of exudates therethrough, such as urine and/or feces (solid, semi-solid, or liquid). The size of at least the primary aperture 80 is important in achieving the desired waste encapsulation performance. If the primary aperture 80 is too small, the waste may not pass through the aperture, either due to poor alignment of the waste source and the aperture location or due to fecal masses having a diameter greater than the aperture 80. If the aperture 80 is too large, the area of skin that may be contaminated by "rewet" from the article is increased. Typically, the aperture 80 should have an area of between about 10 cm$^2$ and about 50 cm$^2$. The aperture 80 preferably has an area of between about 15 cm$^2$ and 35 cm$^2$.

Further, the topsheet 24 may be fully or partially elasticated or may be foreshortened so as to provide a void space between the topsheet 24 and the core 28. Exemplary structures including elasticized or foreshortened topsheets are described in more detail in U.S. Pat. No. 4,892,536 issued to DesMarais et al. on Jan. 9, 1990 entitled "Absorbent Article Having Elastic Strands"; U.S. Pat. No. 4,990,147 issued to Freeland on Feb. 5, 1991 entitled "Absorbent Article With Elastic Liner For Waste Material Isolation"; U.S. Pat. No. 5,037,416 issued to Allen et al. on Aug. 6, 1991 entitled "Disposable Absorbent Article Having Elastically Extensible Topsheet"; and U.S. Pat. No. 5,269,775 issued to Freeland et al. on Dec. 14, 1993 entitled "Trisection Topsheets For Disposable Absorbent Articles and Disposable Absorbent Articles Having Such Trisection Topsheets"; each of which are incorporated by reference herein.

The topsheet 24 is preferably compliant, soft feeling, and non-irritating to the wearer's skin. Further, at least a portion of the topsheet 24 is liquid previous, permitting liquids to readily penetrate through its thickness. At least a portion of the topsheet 24 may be impermeable to liquids and solids or semi-solids or may be permeable to exudates only in a direction away from the wearer. Further, the topsheet 24 may include regions of differing permeability. For example, the topsheet 24 may be liquid permeable in the urine loading region of the diaper (generally front waist region and/or crotch region) and may be impermeable in other areas (e.g., in the area surrounding an aperture 80). Such configuration may provide good urine acquisition characteristics while preventing feces which pass through the aperture 80 from passing back towards the wearer's skin. The topsheet 24 may additionally comprise a multiplicity of secondary apertures as described in more detail in U.S. Pat. No. 5,342,338 issued to Roe on Aug. 30, 1994 entitled "Disposable Absorbent Article For Low-Viscosity Fecal Material". These secondary apertures generally each have an area which is less than the area of the primary aperture but provide a means for low viscosity bodily wastes to penetrate the topsheet 24 if the wastes contact the topsheet 24 in a region other than that of the primary aperture 80.

A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. If the topsheet includes fibers, the fibers may be spunbond, carded, wet-laid, meltblown, hydroentangled, or otherwise processed as is known in the art. One suitable topsheet 24 comprising a web of staple length polypropylene fibers is manufactured by Veratec, Inc., a Division of International Paper Company, of Walpole, Mass. under the designation P-8.

Suitable formed film topsheets are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; and U.S. Pat. No. 5,006,394 "Multilayer Polymeric Film" issued to Baird on Apr. 9, 1991. Other suitable topsheets are made in accordance with U.S. Pat. Nos. 4,609,518 and 4,629,643 which issued to Curro et al. on Sep. 2, 1986 and Dec. 16, 1986, respectively, and both of which are incorporated herein by reference.

Such formed films are available from The Procter & Gamble Company of Cincinnati, Ohio as "DRI-WEAVE" and from Tredegar Corporation of Terre Haute, Indiana as "CLIFF-T."

Preferably, at least a portion of the topsheet 24 is made of a hydrophobic material or is treated to be hydrophobic in order to isolate the wearer's skin from liquids contained in the absorbent core 28. If the topsheet 24 is made of a hydrophobic material, preferably is at least a portion of the upper surface of the topsheet 24 is treated to be hydrophilic so that liquids will transfer through the topsheet more rapidly. The topsheet 24 can be rendered hydrophilic by treating it with a surfactant or by incorporating a surfactant into the topsheet. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991. A more detailed discussion of some suitable methods for incorporating surfactant in the topsheet can be found in U.S. Statutory Invention Registration No. H1670, published on Jul. 1, 1997 in the names of Aziz et al. Each of these references is hereby incorporated by reference herein. Alternatively, the topsheet 24 may include an apertured web or film which is hydrophobic. This may be accomplished eliminating the hydrophilizing treatment step from the production process and/or applying a hydrophobic treatment to the topsheet 24, such as a polytetraflouroethylene compound like SCOTCHGUARD or a hydrophobic lotion composition, as described below. In such embodiments, it is preferred that the apertures be large enough to allow the penetration of aqueous fluids like urine without significant resistance.

Any portion of the topsheet 24 may be coated with a lotion as is known in the art. Examples of suitable lotions include those described in U.S. Pat. No. 5,607,760 entitled "Disposable Absorbent Article Having A Lotioned Topsheet Containing an Emollient and a Polyol Polyester Immobilizing Agent" which issued to Roe on Mar. 4, 1997; U.S. Pat. No. 5,609,587 entitled "Diaper Having A Lotion Topsheet Comprising A Liquid Polyol Polyester Emollient And An Immobilizing Agent" which issued to Roe on Mar. 11, 1997; U.S. Pat. No. 5,635,191 entitled "Diaper Having A Polysiloxane Emollient" which issued to Roe et al. on Jun. 3, 1997; and U.S. Pat. No. 5,643,588 entitled "Diaper Having A Lotioned Topsheet" which issued to Roe et al. on Jul. 1, 1997. The lotion may function alone or in combination with another agent as the hydrophobizing treatment described above. The topsheet may also include or be treated with antibacterial agents, some examples of which are disclosed in PCT Publication No. WO 95/24173 entitled "Absorbent Articles Containing Antibacterial Agents in the Topsheet For Odor Control" which was published on Sep. 14, 1995 in the name of Theresa Johnson. Further, the topsheet 24, the backsheet 26 or any portion of the topsheet or backsheet may be embossed and/or matte finished to provide a more cloth like appearance.

The absorbent core 28 may comprise any absorbent material which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 28 may also be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures). Exemplary absorbent structures for use as the absorbent core are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735, entitled "High Density Absorbent Members Having Lower Density and Lower Basis Weight Acquisition Zones", issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" which issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997. Each of these patents is incorporated herein by reference.

The diaper 20 may also include a sublayer disposed between the topsheet 24 and the backsheet 26. The sublayer may be any material or structure capable of accepting, storing or immobilizing bodily exudates. Thus, the sublayer may include a single material or a number of materials operatively associated with each other. Further, the sublayer may be integral with another element of the diaper 20 or may be one or more separate elements joined directly or indirectly with one or more elements of the diaper 20. Further, the sublayer may include a structure that is separate from the core 28 or may include or be part of at least a portion of the core 28.

Suitable materials for use as the sublayer may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. (As used herein, the term "microporous" refers to materials which are capable of transporting fluids by capillary action. The term "macroporous" refers to materials having pores too large to effect capillary transport of fluid, generally having pores greater than about 0.5 mm in diameter and more specifically, having pores greater than about 1.0 mm in diameter.) One embodiment of a storage element includes a mechanical fastening loop landing element, having an uncompressed thickness of about 1.5 millimeters available as XPL-7124 from the 3M Corporation of Minneapolis, Minn. Another embodiment includes a 6 denier, crimped and resin-bonded nonwoven highloft having a basis weight of 110 grams per square meter and an uncompressed thickness of 7.9 millimeters which is available from the Glit Company of Wrens, Ga. Other suitable absorbent and nonabsorbent storage elements are described in European Patent Application No. EP 0 847 738 A1 entitled "Disposable Absorbent Article Having Capacity to Store Low-Viscosity Fecal Material" published Jun. 17, 1998 in the name of Roe, which is hereby incorporated by reference herein. Further, the sublayer, or any portion thereof, may include or be coated with a lotion or other known substances to add, enhance or change the performance or other characteristics of the element.

The diaper 20 may also comprise at least one elastic waist feature 34 that helps to provide improved fit and containment. The elastic waist feature 34 is generally intended to elastically expand and contract to dynamically fit the wearer's waist. The elastic waist feature 34 preferably extends at least longitudinally outwardly from at least one waist edge of the absorbent core 28 and generally forms at least a portion of the end edge 52 of the diaper 20. Disposable diapers are often constructed so as to have two elastic waist features, one positioned in the first waist region 36 and one positioned in the second waist region 38. Further, while the elastic waist feature 34 or any of its constituent elements may comprise one or more separate elements affixed to the diaper 20, the elastic waist feature 34 may be constructed as an extension of other elements of the diaper 20, such as the backsheet 26, the topsheet 24, or both the backsheet 26 and the topsheet 24.

The elastic waist feature 34 may be constructed in a number of different configurations including those described in U.S. Pat. No. 4,515,595 issued to Kievit et al. on May 7, 1985; U.S. Pat. No. 4,710,189 issued to Lash on Dec. 1, 1987; U.S. Pat. No. 5, 151,092 issued to Buell on Sep. 9, 1992; and U.S. Pat. No. 5,221,274 issued to Buell on Jun. 22, 1993. Other suitable waist configurations may include waistcap features such as those described in U.S. Pat. No. 5,026,364 issued to Robertson on Jun. 25, 1991 and U.S.

Pat. No. 4,816,025 issued to Forema is above mentioned references are incorporated herein by reference.

The diaper 20 may also include a fastening system 40. The fastening system 40 preferably maintains the first waist region 36 and the second waist region 38 in a configuration so as to provide lateral tensions about the circumference of the diaper 20 to hold the diaper 20 on the wearer. The fastening system 40 preferably comprises tape tabs and/or hook and loop fastening components, although any other known fastening means are generally acceptable. Some exemplary fastening systems are disclosed in U.S. Pat. No. 3,848,594 entitled "Tape Fastening System for Disposable Diaper" issued to Buell on Nov. 19, 1974; U.S. Pat. No. B1 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fasterner Portion" issue to Nestegard on Jan. 16, 1990; U.S. Pat. No. 4,946,527 entitled "Pressure-Sensitive Adhesive Fastener And Method of Making Same" issued to Battrell on Aug. 7, 1990; and the herein before referenced U.S. Pat. No. 5,151,092 issued to Buell on Sep. 9, 1992; and U.S. Pat. No. 5,221,274 issued to Buell on Jun. 22, 1993. Another exemplary fastening system is disclosed in co-pending U.S. application Ser. No. 09/143,184 entitled "Absorbent Article Fastening Device" in the names of Kline et al. filed on Aug. 28, 1998. The fastening system may also provide a means for holding the article in a disposal configuration as disclosed in U.S. Pat. No. 4,963,140 issued to Robertson et al. on Oct. 16, 1990. The fastening system may also include primary and secondary fastening systems, as disclosed in U.S. Pat. No. 4,699,622 to reduce shifting of overlapped portions or to improve fit as disclosed in U.S. Pat. Nos. 5,242,436; 5,499,978; 5,507,736; 5,591,152. Each of these patents is incorporated herein by reference. In alternative embodiments, opposing sides of the garment may be seamed or welded to form a pant. This allows the article to be used as a pull-on diaper or training pant.

The diaper 20 may also comprise side panels 30. The side panels 30 may be elastic or extensible to provide a more comfortable and contouring fit. The diaper 20 may be provided with side panels 30 disposed in the first waist region 36 or in both the first waist region 36 and the second waist region 38. The side panels 30 may be constructed in any suitable configurations. Examples of diapers with elasticized side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151,092 issued to Buell on Sep. 9, 1992; and U.S. Pat. No. 5,221,274 issued to Buell on Jun. 22, 5,669,897 issued to LaVon, et al. on Sep. 23, 1997 entitled "Absorbent Artic Providing Sustained Dynamic Fit"; U.S. Pat. application Ser. No. 08/155,048 entitled "Absorbent Article With Multi-Directional Extensible Side Panels" filed Nov. 19, 25 1993 in the names of Robles, et al.; each of which names of Robles, er al.; each of which is incorporated herein by refernce.

The diaper 20 preferably further includes leg cuffs 32 which provide improved containment of liquids and other body exudates. Leg cuffs may also be referred to as leg bands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. on Feb. 28, 1989 and Mar. 20, 1990, respectively, describe disposable diapers having "stand-up" elasticized flaps (barrier cuffs) which improve the containment of the leg regions. U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs and barrier cuffs. In some embodiments, it may be desirable to treat all or a portion of the leg cuffs with a lotion, as described above.

Embodiments of the present invention may also include pockets for receiving and containing waste, spacers which provide voids for waste, barriers for limiting the movement of waste in the article, compartments or voids which accept and contain waste materials deposited in the diaper, and the like, or any combinations thereof. Examples of pockets and spacers for use in absorbent products are described in U.S. Pat. No. 5,514,121 issued to Roe et al. on May 7, 1996, entitled "Diaper Having Expulsive Spacer"; U.S. Pat. No. 5,171,236 issued to Dreier et al on Dec. 15, 1992, entitled "Disposable Absorbent Article Having Core Spacers"; U.S. Pat. No. 5,397,318 issued to Dreier on Mar. 14, 1995, entitled "Absorbent Article Having A Pocket Cuff"; U.S. Pat. No. 5,540,671 issued to Dreier on Jul. 30, 1996, entitled "Absorbent Article Having A Pocket Cuff With An Apex"; and PCT Application WO 93/25172 published Dec. 3, 1993, entitled "Spacers For Use In Hygienic Absorbent Articles And Disposable Absorbent Articles Having Such Spacer"; and U.S. Pat. No. 5,306,266, entitled "Flexible Spacers For Use In Disposable Absorbent Articles", issued to Freeland on Apr. 26, 1994. Examples of compartments or voids are disclosed in U.S. Pat. No. 4,968,312, entitled "Disposable Fecal Compartmenting Diaper", issued to Khan on Nov. 6, 1990; U.S. Pat. No. 4,990,147, entitled "Absorbent Article With Elastic Liner For Waste Material Isolation", issued to Freeland on Feb. 5, 1991; U.S. Pat. No. 5,62,840, entitled "Disposable Diapers", issued to Holt et al on Nov. 5, 1991; and U.S. Pat. No. 5,269,755 entitled "Trisection Topsheets For Disposable Absorbent Articles And Disposable Absorbent Articles Having Such Trisection Topsheets", issued to Freeland et al on Dec. 14, 1993. Examples of suitable transverse barriers are described in U.S. Pat. No. 5,554,142 entitled "Absorbent Article Having Multiple Effective Height Transverse Partition" issued Sep. 10, 1996 in the name of Dreier et al.; PCT Pat. WO 94/14395 entitled "Absorbent Article Having An Upstanding Transverse Partition" published Jul. 7, 1994 in the name of Freeland, et al.; and U.S. Pat. No. 5,653,703 Absorbent Article Having Angular Upstanding Transverse Partition, issued Aug. 5, 1997 to Roe, et al. All of the above-cited references are hereby incorporated by reference herein.

Preferably, the diaper 20 includes a water-activatable adhesive 90 or body adhering composition which acts to hold the article or some portion thereof in place during use. The water-activatable adhesive 90 preferably maintains the article or a portion thereof in coordination with a specific area of the wearer's anatomy during use. For example, the longitudinal, lateral, and/or the z-directional placement of the article may be maintained by the activatable topical adhesive 90. Alternatively, the adhesive 90 may be used to adhere a portion of the article to another portion of the article or a different article. The water-activatable adhesive may also be used as a disposal means for holding the article in a proper configuration for disposal after use.

The water-activatable adhesive is preferably substantially anhydrous. For the purposes of the present invention, the term "substantially anhydrous" refers to a water content of the water-activatable adhesive in its unactivated or "pre-activated" state of less than about 5 percent by weight of the adhesive.

The water-activatable adhesive may include a topical adhesive. A topical adhesive, as used herein is defined as an adhesive formulated for use in direct skin contact, such as adhering a bandage or other article to the skin. A water-activatable topical adhesive is an adhesive which exhibits an increase in "tack" or adhesion after being subjected to or contacted with water or a water-containing material such as an aqueous solution.

Preferably, the adhesive force, or adhesion, of the water-activatable adhesive is essentially zero prior to activation. In one preferred embodiment the pre-activation adhesion of the water-activatable adhesive 90 is less than about 10 g/in as measured by the Adhesion Method described below. In another embodiment, the pre-activation adhesion is between about 0.01 g/in and about 100 g/in. Once activated, the adhesive preferably has a sufficient adhesion to perform the intended function (for example, hold an article in contact with the skin). In certain embodiments of the present invention, the water-activatable adhesive 90 may have an unactivated adhesion value measurably greater than zero. In these cases, the adhesive force of the water-activatable adhesive 90 after activation is typically at least about twice that of the adhesive prior to activation. Preferably, the adhesive force of the water-activatable adhesive 90 after activation is typically at least about three times that of the adhesive prior to activation. More preferably, the adhesive force of the water-activatable adhesive 90 after activation is typically at least about five times that of the adhesive prior to activation. Even more preferably, the adhesive force of the water-activatable adhesive 90 after activation is at least 10 times that of the adhesive prior to activation and may be at least about one hundred times that of the adhesive prior to activation. In one preferred embodiment, the post-activation adhesion of the water-activatable adhesive is between about 20 g/in and about 700 g/in, and more preferably between about 50 g/in and 400 g/in.

The elapsed time required for activation of the water-activatable adhesive 90 while in contact with the water or water-containing material is important to performance of the disposable absorbent article of the present invention. The activation should be rapid enough to reduce the likelihood that the product will shift on the wearer before the adhesive has time to activate which could lead to inadvertent adhesion of the article in an undesirable location on the wearer. On the other hand, the activation should be slow enough to prevent inadvertent adhesion of the product to the wearer's or caregiver's skin in an undesirable location during the application process and prior to final positioning of the product. Typically, in preferred adhesive embodiments described in more detail below, the elapsed time required for activation should be between about 2 seconds and about 10 minutes, and preferably between about 5 seconds and about 1 minute. In any case, the time required for activation may be decreased by increasing the surface area-to-mass ratio of the adhesive (e.g., by decreasing the thickness of the adhesive layer or forming "strings" of the adhesive). Conversely, the time required for activation may be increased by decreasing the surface area-to-mass ratio of the adhesive.

Figure 2:
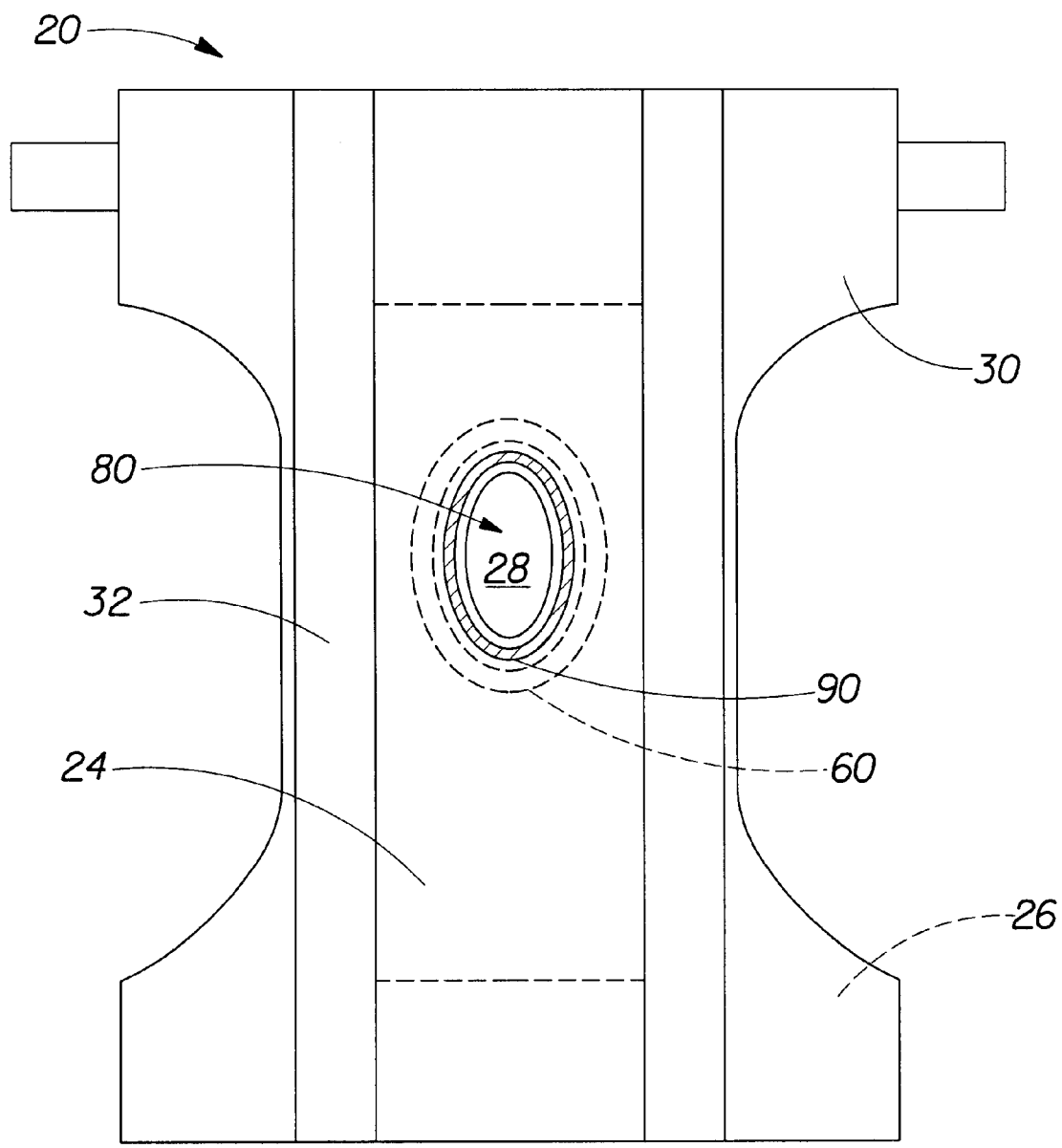
FIG. 2 is a plan view of a disposable diaper configuration of the present invention.

As shown in FIG. 2, the activatable topical adhesive 90 may be located on the topsheet 24. However, the activatable topical adhesive 90 may also be integral with the material making up the topsheet 24 or other element of the absorbent article or may be a separate material disposed directly or indirectly on all or any portion of the absorbent article.

Further, the activatable topical adhesive 90 may be disposed on any portion of the absorbent article in any pattern or configuration including, but not limited to lines, stripes, dots, and the like. For example, in FIG. 9, the water-activatable adhesive 90 is shown in the waist and/or leg cuff regions of the article 20. Further, the activatable adhesive may be used to provide attachment between different parts of the article or between two or more different articles.

The activatable topical adhesive 90 should be non-irritating and generally compatible with human skin. The in-use tack or adhesion level should be sufficient so as to be able to maintain coordination with the wearer's anatomy, but not so aggressive so as to be unduly difficult or painful to remove from the skin.

As described above, the water-activatable topical adhesive 90 is preferably activated by water present during the application or wearing of the article. The activating water may be pure water or another aqueous media, such as sweat, urine, feces, transepidermal water (i.e., water normally lost from the body through the skin), residual water from bathing or use of water-based disposable wet wipes, or may be supplied from a releasable source within the article. In certain embodiments, the activating aqueous medium is supplied to the adhesive 90 via a closed distribution system at the time of urination.

A "closed system liquid transport member" or "closed distribution system" comprises a liquid filled member having an inlet port and outlet port, which upon receipt of even a little amount of liquid at the inlet port practically immediately releases liquid at the outlet port. Liquid transport through such transport members is based upon direct suction rather than on capillarity. The liquid is transported through a region into which no significant quantity of air (or other gas) may enter. The driving force for liquid flowing through such a member can be created by a liquid sink (e.g., a capillary or osmotic absorbent structure) or source in liquid connection with the member. Thus, a liquid transport member should have a relatively high liquid permeability.

There are preferably at least two regions within the transport member with different pore sizes, namely the one or more port region(s) having smaller pores and the inner region having a much larger pore size. The inner region of the transport member has a permeability that is relatively high compared to the permeability of a port region (a higher liquid permeability provides less flow resistance), which can be a part of an outer/wall region circumscribing the inner/bulk region. Nonlimiting examples of high porosity materials suitable for use as the inner region material include fibrous structures comprising polyolefin, PET, cellulose, and cellulose-based fibers, and porous, open celled foam such as reticulated foams, cellulose sponges, polyurethane foams, and HIPE foams. In one embodiment, the voids of the inner region are essentially completely filled with an essentially incompressible fluid. The term "essentially completely" refers to the situation, where sufficient void volume of the inner region is filled with the liquid such that a continuous flow path between inlet and outlet ports can be established.

The port regions of the transport member comprise materials which are permeable for the transport liquid, but not for the ambient gas (like air) once they are wetted with the transport liquid. Often, such materials are described as membranes, which are defined as regions that are permeable for liquid, gas or a suspension of particles in a liquid or gas. The membrane may for example comprise a microporous region to provide liquid permeability through the capillaries. In an alternative embodiment, the membrane may comprise a monolithic region comprising a block-copolymer through which the liquid is transported via diffusion. Exemplary membranes for the port regions include celluloseacetate membranes, such as also disclosed in U.S. Pat. No. 5,108, 383 entitled "Membranes for Absorbent Articles" issued to White on Apr. 28, 1992, PET films as disclosed in EP-A-0451797, nitrocellulose membranes, cellulosenitrate membranes, PTFE membranes, polyamide membranes, and polyester. Other suitable materials are woven polymeric meshes, such as polyamide or polyethylene meshes as available from Verseidag in Geldern-Waldbeck, Germany, or SEFAR in Ruschlikon, Switzerland.

Suitable water activated adhesives include denture adhesives, denture adhesive laminates, gums, and water swellable binders. One example of a water activatable denture adhesives laminate is SeaBond® denture adhesive available in wafers from COMBE Incorporated of White Plains, N.Y. Additional denture stabilizing compositions may include Gantrez polymers, carboxymethylcellulose, karaya gum, sodium alginate, polyethylene oxide, and polyethylene glycol. One preferred denture stabilizing composition is described in U.S. Pat. No. 5,658,586. Other suitable water-activated adhesives are described in U.S. Pat. Nos. 5,686,180 and 5,202,181.

It has been found that water-activated curable binding resins such as Vinnex LL572 (from Wacker Polymer Systems of Adrian, Mich.) may be employed as water-activated adhesives. These resins may be attached to a carrier element such as a synthetic fiber nonwoven web by wetting them slightly with water and subsequently heating the laminate to partially cure the resin, thereby affixing it to the carrier element. For example, 0.024 g/cm 2 of water may be sprayed onto a nonwoven (e.g., P-8 spunbond polypropylene available from the FiberTech Group, Inc. of Landisville, N.J.). To the wetted nonwoven, 0.008 g/cm 2 of the Vinnex LL572 resin may be evenly applied. The laminate is then heated in an oven at 210 degrees C. for 30 seconds to produce the water-activatable adhesive laminate.

The water-activatable adhesive 90 may be disposed on any portion of the article intended to be adhered to a wearer or another portion of the article or a different article.

In one embodiment, as shown in FIG. 2, the water-activatable adhesive 90 may be located on the topsheet 24 of the article 20. However, the water activatable adhesive 90 may also be integral with the material making up the topsheet 24 or other element of the absorbent article or may be a separate material disposed directly or indirectly on all or any portion of the absorbent article. Further, the water-activatable topical adhesive 90 may be disposed on any portion of the absorbent article. For example, in FIG. 9, the water-activatable adhesive 90 is shown in the waist and leg cuff regions of the article 20. The water-activatable adhesive may be put on the article by any means and may be in any pattern or configuration including, but not limited to, lines, stripes, dots, and the like.

Certain preferred embodiments of the present invention are particularly suited to the entrapment or encapsulation of bodily waste and thus reduce the amount and area of contamination of the wearer's skin by the waste. In order to achieve the desired level of performance, especially for viscous bodily waste such as feces, at least two functions should be performed. First, the diaper should have means of maintaining proximity of the accepting element of the diaper (e.g., an aperture in the topsheet) to the wearer's waste exit point (e.g., anus) of the wearer. By "aperture" it is meant any opening in the topsheet that may allow passage of waste from the wearer facing side to the garment facing side of the topsheet, including holes of any shape, slits and the like. The topsheet may also include elastic means suitable for foreshortening the topsheet in the longitudinal and/or other dimensions. Second, the diaper should provide a void space 70 for the waste even under applied pressures which are typical of those generated by a wearer on the crotch and buttocks regions of the article while the wearer is in a seated position. Both of these functions can be performed, for example, by a diaper as depicted in FIG. 2 which includes an apertured topsheet, spacing member and an adhesive to maintain the aperture in the region of the wearer's anus.

Figure 3:
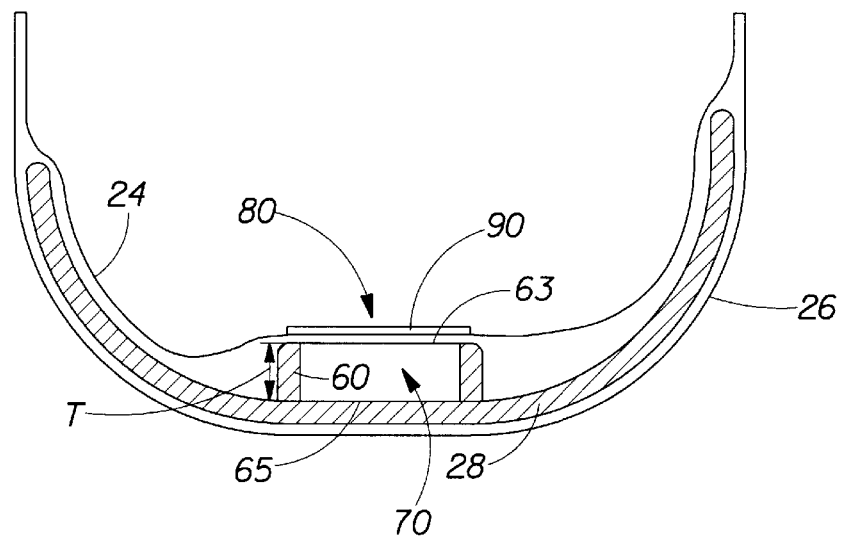
FIG. 3 is a cross-sectional view of one embodiment of the present invention shown as it may appear when worn.

In one preferred embodiment, as shown in FIGS. 2–3, the water-activatable is topical adhesive 90 may be disposed on the topsheet 24 around the entire perimeter of the aperture 80. However, embodiments are contemplated wherein the activatable topical adhesive 90 surrounds only a portion of the aperture 80 and/or is disposed in locations not directly adjacent the aperture 80, such as around the edge of the topsheet 24, on the leg cuffs 32 or in one or both of the waist regions. Alternatively, activatable topical adhesive 90 may be disposed on a spacer 60. If this is done, the activatable topical adhesive 90 may be on an exposed surface of the spacer 60 or may be located beneath an apertured, slit or otherwise reticulated layer such that the activatable topical adhesive 90 can contact the wearer in use. In any case, the effectiveness of the water-activation process may be enhanced by increasing the surface area to unit mass ratio (e.g., via thin films, foams, etc.).

In certain embodiments, one or more spacers 60 may be used to provide a void space 70 which can be maintained under pressures which are typical of those generated by a wearer on the crotch and buttocks regions of the article while the wearer is in a seated position. The spacing member(s) 60 are intended to space the topsheet 24 or other covering layer away from the absorbent core 28 and/or other underlying layers such as sublayers, acquisition layers and the like. However, it is also contemplated that the spacing member 60 may space apart any other two elements of the diaper 20, including but not limited to the topsheet 24 and the backsheet 26, the acquisition layer and the core 28, the core 28 and the backsheet 26, etc. Nonlimiting, exemplary spacers 60 are disclosed in the patents incorporated by reference above.

The spacing member 60 may be of any suitable size and/or shape. In preferred embodiments, the spacing member 60 has a body facing side 62, a backsheet facing side 64 and a thickness T of between about 0.5 cm and about 3.0 cm in use. (As used herein, the thickness T of the spacer 60 is the distance between the body facing side 63 and the garment facing side 65 of the spacer 60.) Further, it is preferred that the spacer 60 create and maintain during use a void space 70 of between at least about 10 cubic cm and about 150 cubic cm, and preferably between about 25 cubic cm and about 75 cubic cm. It is also important that the lateral dimension X of the void space 70 be large enough to accommodate the feces, but narrow enough such that the spacing member 60 can support the ischia of the wearer. Preferably, the lateral dimension X of the void space 70, defined by the spacer 60 in the area corresponding to the anus of the wearer, is between about 1 cm and about 5 cm, and more preferably between about 1.5 cm and about 3.5 cm.

Figure 4:
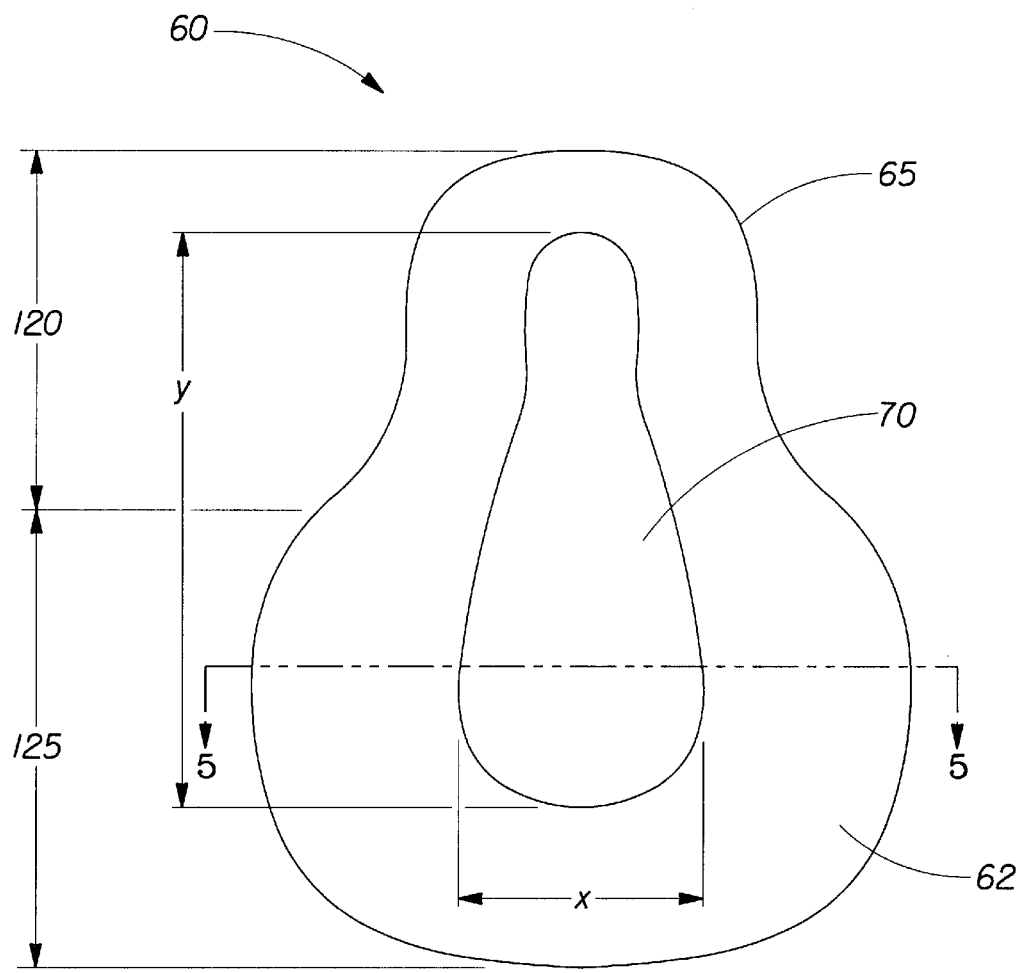
FIG. 4 is a plan view of a spacing member suitable for use with the present invention.
Figure 5:
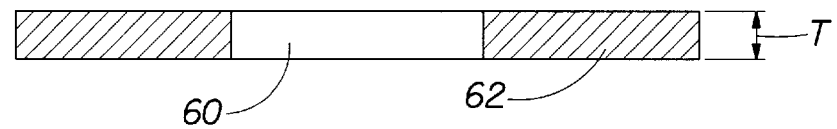
FIG. 5 is a cross-sectional view of the spacing member shown in FIG. 4 taken through section line 5—5.
Figure 6:
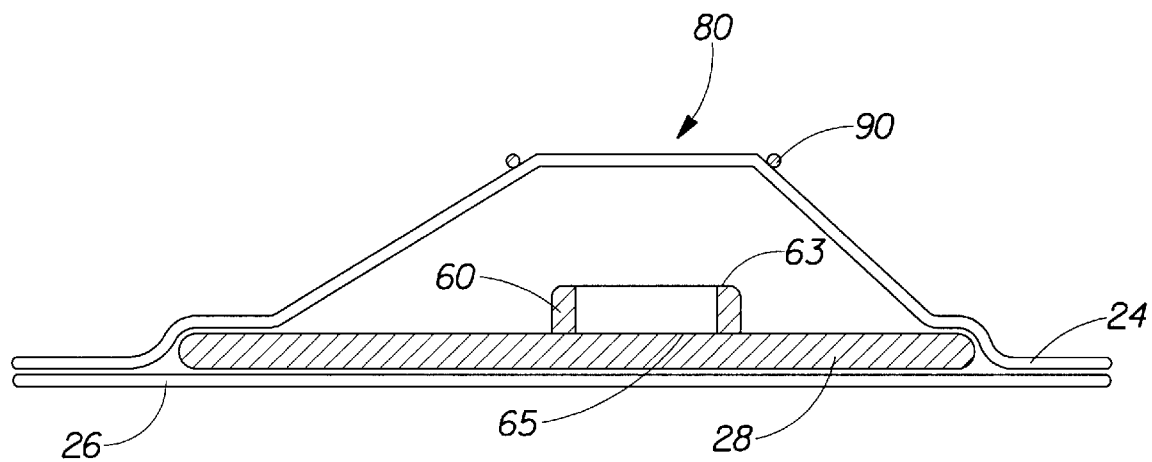
FIG. 6 is a cross-sectional view of one embodiment of the present invention.

Although the shape of the spacer 60 is not critical, it has been found that elliptical and "keyhole" shaped spacers (e.g. the spacer shown if FIG. 4) perform particularly well. If such a spacer 60 is implemented, it is preferred that the spacer 60 be disposed generally in the crotch region 37 of the diaper 20 and oriented such that the first region 120 of the spacer 60 is located toward the front waist of the diaper 20 when worn and the second region 125 of the spacer 60 is located toward the rear waist of the diaper 20 when worn. Alternatively, U-shaped spacers may be suitable for use in certain embodiments (preferably with the open end of the U-shape oriented toward the rear waist region of the diaper 20 when worn). In any case, the spacer 60 may be unitary or may comprise a multiplicity of separate or operatively associated parts. Further, the spacer 60 may have a closed perimeter 65 or may comprise openings, holes, or channels extending from the fecal void space 70 through the spacer wall 62 to the perimeter 65 of the spacer 60. Such embodiments may be useful to allow distribution of feces from the void space 70 to other parts of the diaper 20.

The spacing member 60 may comprise any material or combination of materials which are suitable for use in an absorbent article to be worn by a human wearer. For example, the spacing member 60 may include foams, woven or nonwoven webs, thermoplastic materials, organic materials, fibers, gels, rubber or synthetic rubber, etc. In one preferred embodiment, the spacing member 60 comprises an absorbent foam made from a 16:1 water/oil emulsion, having a glass transition temperature of about 10° C., and having a compression of about 40% in a dry state and about 30% in a wet state (i.e., when Io saturated with water) under about 1.0 psi applied pressure. Thus, in certain embodiments, the compression under about 1.0 psi in the wet state may be less than the compression under about 1 psi in the dry state.

In a preferred embodiment, the spacing member 60 is relatively soft, but resilient and capable of withstanding the forces typical of a baby's movements and/or the weight of a baby sitting or lying on the spacing member 60. Thus, the spacing member 60 should be capable of withstanding at least 0.5 psi and preferably at least about 1.0 psi while compressing no more than about 60%, and preferably no more than about 30% in both wet and dry conditions.

In yet another embodiment, the spacing member 60 may be activatable during use. That is, the spacing member 60 may be stored in the diaper 20 in one configuration and may be activated by some event or material which changes the configuration of the spacing member 60 or the surrounding structure so as to provide the diaper 20 with a desired configuration for receiving and/or storing bodily exudates. For example, the spacing member 60 may include a material which expands when contracted by water, urine, feces, enzymes or other means associated with the wearer's body or bodily exudates. Changes in temperature, pH and saline concentration are also "triggers" which can activate the spacing member 60. Thus, when the wearer urinates, the spacing member 60 may increase in thickness, change shape or otherwise orient itself in the diaper 20 to provide a void space 70 into which urine and/or feces can flow.

In preferred embodiments, at least a portion of the spacing member 60 is joined to the topsheet 24. This helps keep the primary aperture 80 aligned with the void space 70 of the spacer 60 during use. It is also preferred that at least a portion of the spacer 60 be joined with at least a portion of the structure which underlies the spacer 60, such as the core 28, a sublayer or the backsheet 28. In any case, the spacer 60 may be joined directly or indirectly by any means known in the art. Typical joining means include adhesives, heat, pressure, static, magnetism, snaps, hook and loop fasteners and the like. The advantages of a diaper including an apertured topsheet and a spacing member 60 are significantly reduced if the aperture 80 does not stay aligned with the wearer's anus and the void space 70 provided by the spacer 60 throughout the time of use (or at least until the wearer has a bowel movement). Accordingly, the diaper 20 of the present invention is preferably provided with a means for maintaining the aperture 80 in alignment with the wearer's anus.

In some embodiments, a water-activatable adhesive 90 may be used to attach at as least a portion of the article to the wearer while the caregiver connects a primary fastening system. In such embodiments, the water-activatable adhesive 90 is preferably disposed near the laterally outboard portion of the back or front waist region of a diaper. To apply the article, the caregiver may activate the adhesive and place the portion of article including the activatable adhesive against a predetermined portion of the wearer's skin. (For example, the adhesive may be applied adjacent the wearer's back waist region, the wearer's hips, and/or the wearer's buttocks.) The caregiver then configures the remainder of the article about the wearer and fastens the primary fastening system of the article.

In other embodiments, the water-activatable adhesive 90 may be a topical adhesive which provides improved fit of the product during wearing by providing at least some additional resistance to the diaper slipping downward or moving in other undesirable ways during use (i.e., providing a higher effective coefficient of friction between the product (i.e., adhesive) and the wearer's skin). In these embodiments, the wateractivatable adhesive 90 may be located on any body-contacting surface of the product.

Some preferred locations for the water-activated adhesives are disclosed in co-pending U.S. patent application Ser. No. 09/312,997 entitled "Disposable Absorbent Article Having Article Retention Zones" filed May 17, 1999 in the names of Gregory Ashton et. al. as the locations for the garment retention zones. The above identified patent application is hereby incorporated by reference herein.

Figure 10:
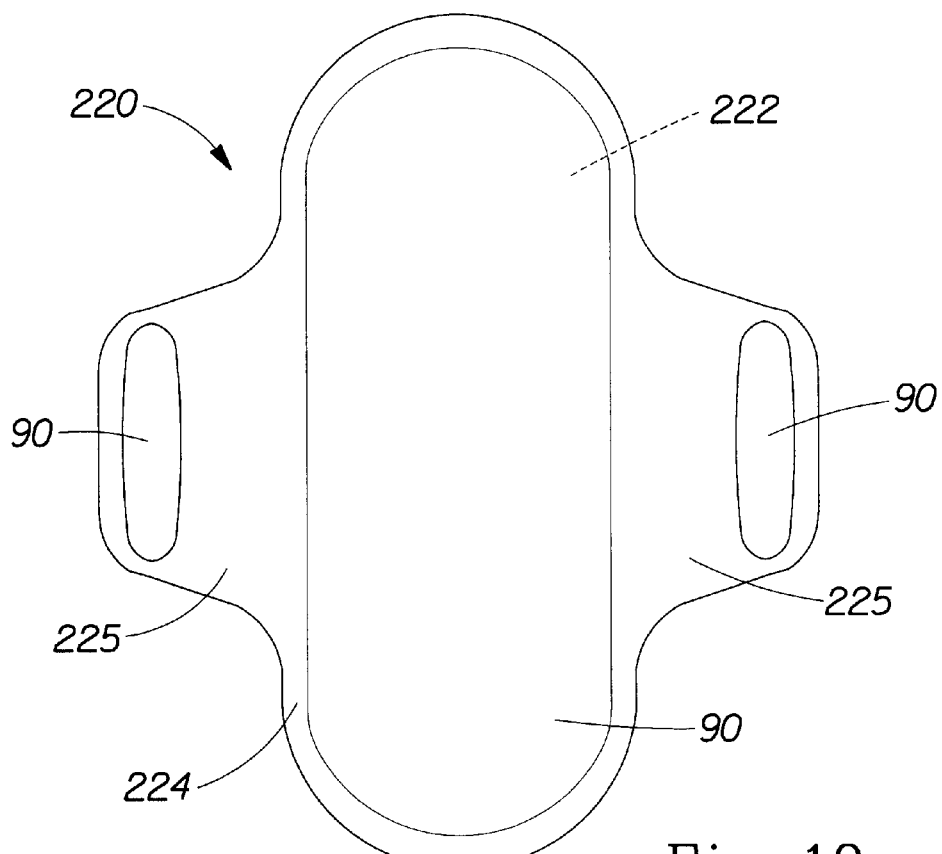
FIG. 10 is a plan view of an alternative embodiment of an absorbent article of the present invention.
Figure 11:
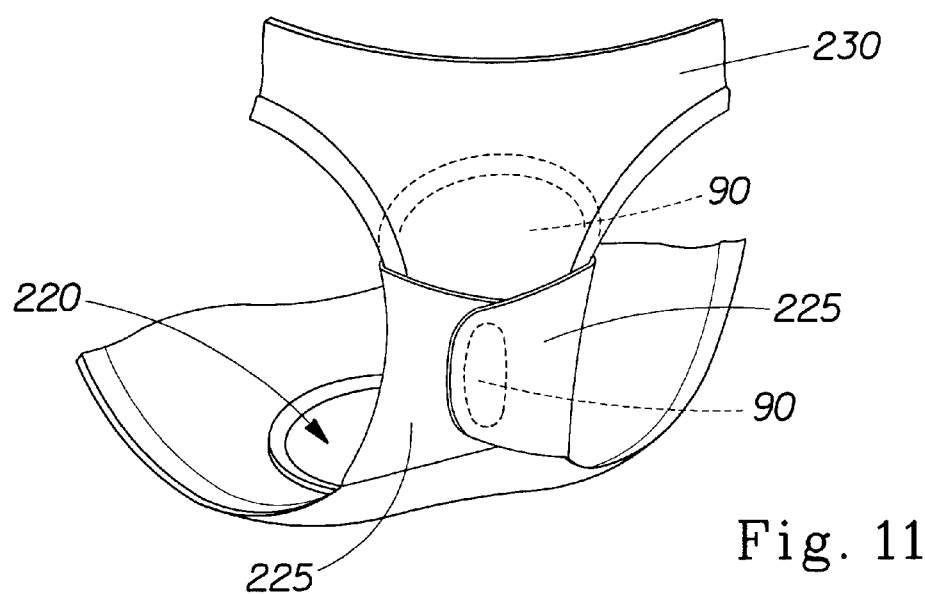
FIG. 11 is a perspective view of the article of FIG. 10 shown as it would be worn by a wearer.
Figure 12:
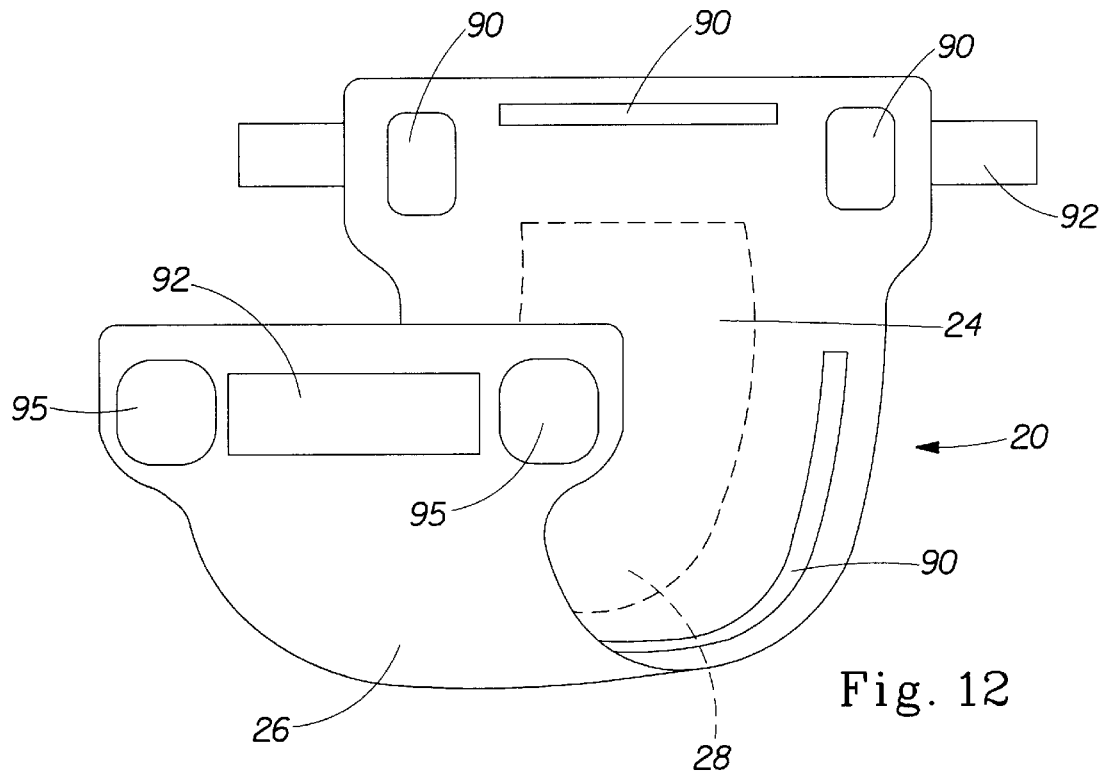
FIG. 12 is a perspective view of one embodiment of the present invention in the form of an absorbent article.

In yet other embodiments, the water-activatable adhesive 90 may serve as the primary or secondary fastening system or a component thereof (see, FIG. 12). For example, the water-activatable adhesive 90 may function as an adhesive tape tab fastener for a diaper. Further, the water-activatable adhesive 90 may be used in conjunction with a sanitary napkin or other feminine protective device. One such device is shown in FIGS. 10 and 11. The sanitary napkin 220 shown has a topsheet 222, a backsheet 224 and wings 225. (It should be noted that the sanitary napkin need not have wings to function in accordance with the present invention.) As shown, the water-activatable adhesive 90 may be disposed in the backsheet 224, the wings 225, or both. The adhesive 90 can act to connect the wings 225 or flaps of the sanitary napkin 220 to each other around the wearer's underwear 230, may alternatively connect the wings 225 or flaps directly to the wearer's underwear 230, may attach the main body of the sanitary napkin to the wearer's underwear 230, or may be used as an adhesive for disposal of the article. In still further embodiments the adhesive 90 may be disposed on the topsheet 222 or other body-facing surface so as to adhere the sanitary napkin 220 directly to the wearer's skin or to another article or device. Typical sanitary napkins are described in U.S. Pat. No. 4,589,876 issued to Van Tilburg, May 1986; 4,687,478 issued to Van Tilburg Aug. 18, 1987; and 5,009,653 issued to Osborn on Apr. 15, 1991. Examples of interlabial feminine protection devices are disclosed in U.S. Pat. No. 5,762,644 issued to Osborn et. al. on Jun. 9, 1998. Each of these patents is incorporated herein by reference.

The water-activatable adhesive may also be used in conjunction with any type of primary fastening system 92 as described herein to supplement its fastening strength, thereby increasing the resistance to removal versus the use of the primary fastener alone. Preferably, in these embodiments, the water-activatable adhesive 90 increases the peel and/or shear strength of the fastener by at least about 10%, more preferably by at least about 25%, even more preferably by at least about 50%, and most preferably by at least about 100%. The activatable adhesive in such embodiments may be part of or separate from the primary system. The water-activated adhesive 90 may be placed laterally inward or laterally outboard of the primary system, longitudinally above or below the primary system 92, or even be coincident or interleaved with the primary system. One exemplary approach to placing the water-activated adhesive 90 coincident with the primary system 92 is disclosed in publications WO 95/25905 and WO 98/10728, each of which is incorporated herein by reference. The water-activated adhesive 90 can replace the cohesive portion of the 2-mechanism mechanical-cohesive system described in WO 95/25905 on either the hook portion, the loop portion, or both portions of the 2-mechanism system. (See, for example, FIG. 12) Alternatively, the water-activated adhesive 90 may replace the bonding element at the base of the loops described in WO 98/10728, which is incorporated by reference herein. Yet another embodiment of coincident systems places one or more regions of water-activated adhesive 90 among one or more other fasteners, examples of which are shown in FIGS. 9A–9E.

In alternative embodiments, the water-activatable adhesive 90 may be used in conjunction with any type of primary fastening system to control the relative position of parts of the article not directly controlled by the primary fastening system. In such fastening systems on a diaper, the water-activated adhesive 90 may reduce shifting of any overlapping portions or components of the diaper or to improve fit. In such embodiments, the water-activated adhesive 90 may be used as the primary fastening system, the secondary fastening system, or for both fastening systems. Likewise, a sanitary napkin may comprise a standard pressure sensitive adhesive for attachment of the pad to the wearer's underwear, and a water-activatable adhesive 90 for attachment of the protective wings to the underwear or a water-activatable adhesive 90 for attachment to the wearer's underwear and a standard pressure sensitive adhesive for attachment of the protective wings to the underwear or each other. Embodiments are also contemplated wherein the water-activatable adhesive 90 functions as the primary fastener, and other fasteners (e.g., pressure sensitive adhesives, mechanical fasteners, etc.) function as a secondary fastener.

In certain embodiments, the water-activatable adhesive 90 may be disposed on the article to adhere a portion of the product to itself. In such cases, the article may include at least one adhesive receiving zone 95, one example of which is shown in FIG. 12. The water-activatable adhesive receiving zone 95 is the location at which the water-activatable adhesive 90 adheres one portion of the article to another portion of the article. The relative positions of the water-activatable adhesive 90 and the adhesive receiving zone 95 can vary. For example, the water-activatable adhesive 90 may be disposed on the body facing surface of the product and the adhesive receiving zone 95 may be disposed on the outer surface of the product. Alternatively the adhesive receiving zone 95 may be disposed on the body facing surface of the product and the water-activatable adhesive 90 may be disposed on the outer surface of the product. Further, the adhesive receiving zone 95 and the water-activatable adhesive 90 may both be disposed on the body facing surface of the product or both be disposed on the outer surface of the product. In any case, the adhesive receiving zone 95 may be a separate piece or material added to the diaper or may be integral to a part of the diaper, including but not limited to the topsheet, the backsheet, the leg cuff, or the waistband.

The water-activatable adhesive 90 may further be employed to help maintain the product in a closed, wrapped configuration for disposal. Embodiments previously disclosed herein in which the water-activatable adhesive 90 is disposed on the body facing surface of the product can readily utilize the water-activatable adhesive 90 for disposal (e.g., the diaper shown in FIG. 12). However, the activatable adhesive may also or alternatively be disposed on the outer surface of the article in a position to maintain the product in a disposal configuration. Further, water-activatable adhesive 90 may be used in place of or along with standard type designs such as with many tape designs to secure the product for disposal, including disposal tape systems disclosed in U.S. Pat. Nos. 5,108,384; 4,869,724; 5,019,065; 5,575,784; 5,626,573; and 5,279,604 and publications WO 98/53780 and WO 99/17693. Each of these patents is incorporated by reference herein.

Figure 7:
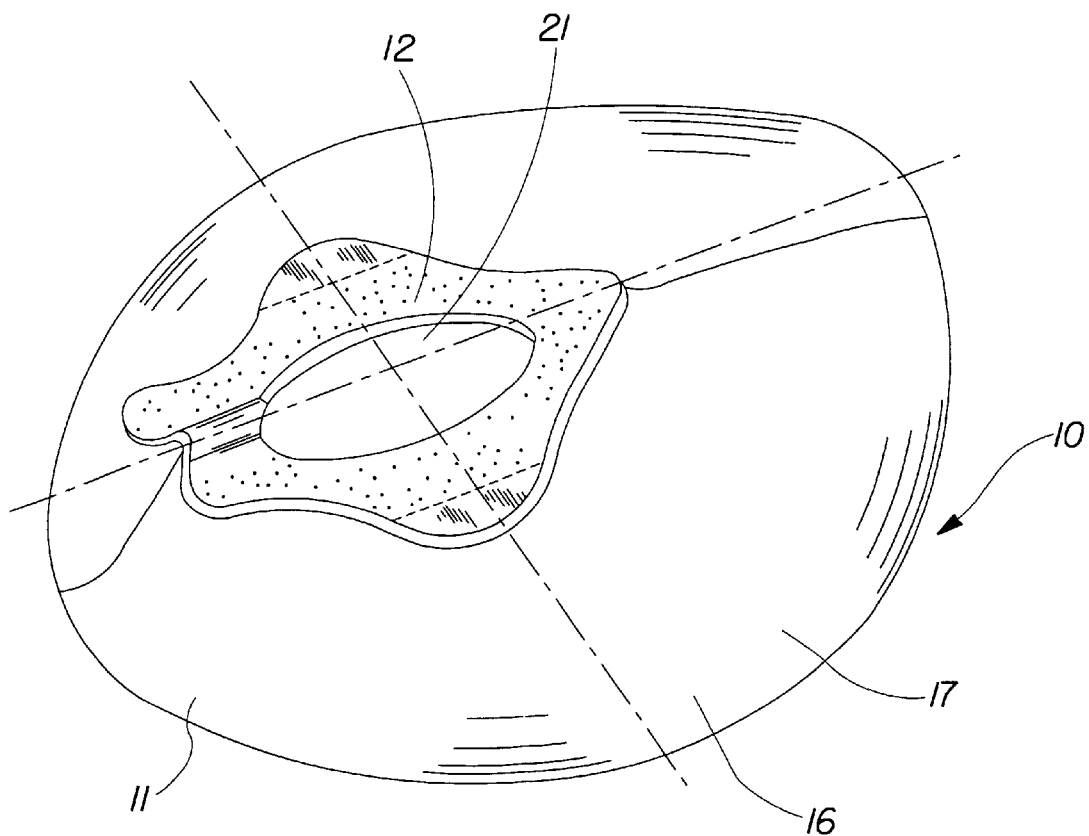
FIG. 7 is a perspective view of one embodiment of a fecal management device.
Figure 8:
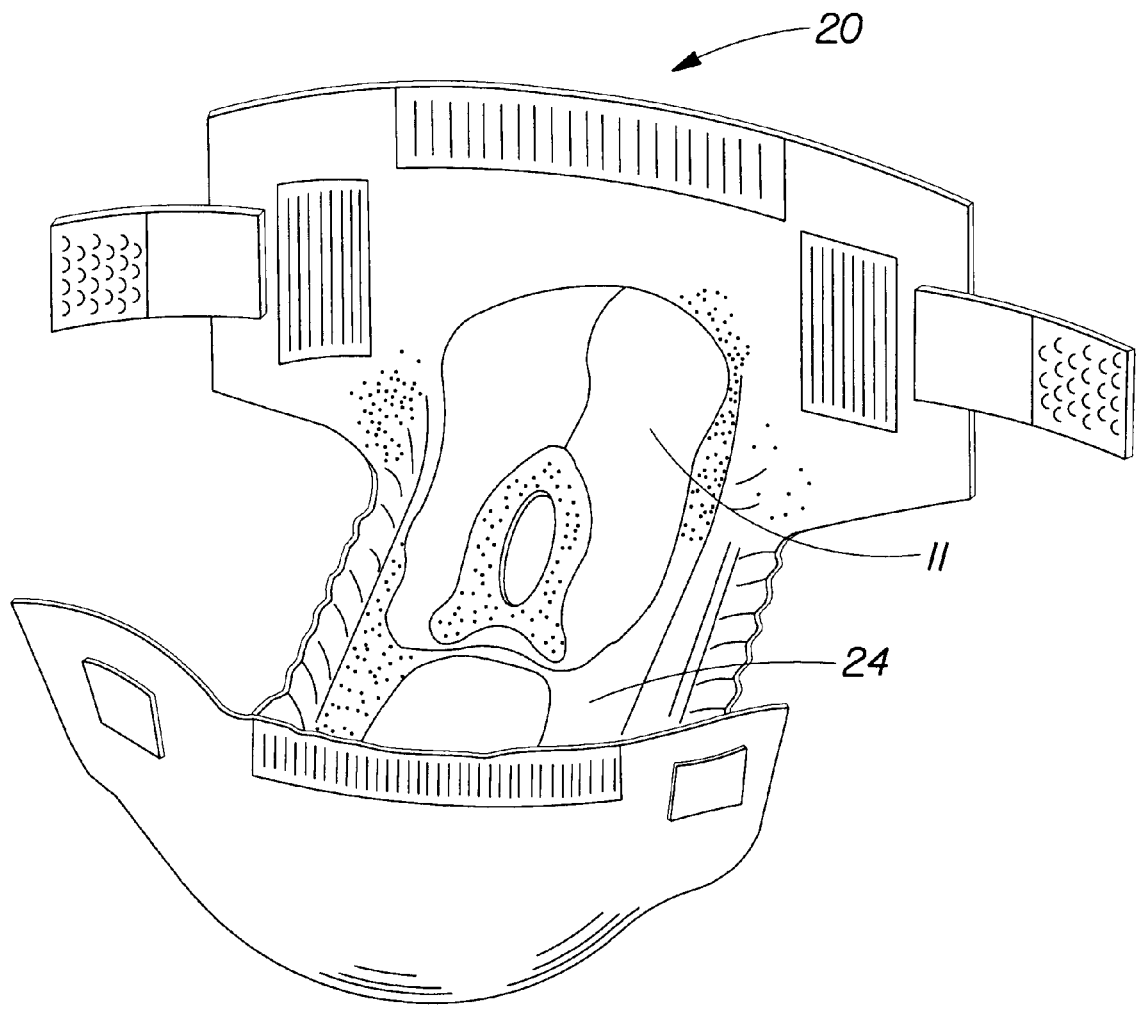
FIG. 8 is a perspective view of a diaper including a fecal management device.

Embodiments of the present invention may also include a waste management device 10 such as is shown in FIG. 7. The waste management device 10 may include a waste bag 11 to collect feces, urine or both. The waste bag 11 may have an aperture 21 and a flange 12 surrounding the aperture for preferably adhesive attachment to the perianal area of a wearer. Further, the waste management device 10 has been found to be particularly useful and beneficial when used in conjunction with a garment, or diaper, preferably a disposable diaper. One example of a diaper 20 including a waste bag 11 is shown in FIG. 8. If associated with a diaper 20 or other garment, the waste bag 11 may be disposed on or joined to any surface of the article. In one embodiment, the waste bag 11 is joined to the topsheet 24 of the diaper 20.

The waste bag 11 is preferably a flexible receptacle for the containment of excreted fecal matter or urine. Thus, the waste bag 11 is preferably liquid impermeable, and yet it may be breathable. Further, the waste bag 11 is designed of sufficient strength to withstand typical wearing conditions, such as sitting.

The waste bag 11 may comprise one or multiple layers. In one embodiment, the waste bag 11 may comprise three layers, preferably one film and two non-woven layers. The layers of the bag material may comprise any material, preferably so that the bag is liquid impervious. In a preferred embodiment of the present invention a laminate may be formed from a non-woven layer and a film. Any non-woven layer can comprise felt fabrics, spunlaced fabrics, fluid jet entangled fabrics, air-laid fabrics, wet-laid fabrics, dry-laid fabrics, melt-blown fabrics, staple fibre carding fabrics, spunbonded fabrics, stitch-bonded fabrics, apertured fabrics, combinations of the above or the like. Further, the non-woven layer or the non-woven layers comprised by the bag material may be hydrophobic or hydrophilic. Typically, the non-woven layer is treated with a surface active material, such as a fluorchemical or other hydrophobic finishings, to provide the requisite hydrophobicity. The non-woven layer, however, may equally be treated with coatings of liquid impervious materials such as hot-melt adhesives or coatings of silicone or other hydrophobic compounds such as rubbers and vegetable and mineral waxes or it may be physically treated using nano-particulates or plasma coating techniques, for example.

The non-woven layer may also be treated with agents to improve the tactile perceivable softness of the waste bag 11. The agents may include but are not limited to vegetable, animal or synthetic oils, silicone oils and the like. Additionally, surfactant materials, including anionic, non-anionic, cationic and non-cationic surfactants may be added to further enhance softness and surface smoothness. Furthermore, the non-woven layer may be impregnated with a lotion to provide desirable therapeutic or protective coating lotion benefits. The lotion coating on the waste bag 11 is preferably transferable to the skin of the wearer by normal contact and wearer motion and/or body heat. It is also possible to impregnate the non-woven layer with a solid oil phase of cream formulation or to incorporate into the non-woven layer an array of pressure- or thermal- or hydrorupturable capsules containing for example, baby oil.

Suitable film materials for any of the film layers preferably comprise a thermoplastic material. The thermoplastic material can may be vapor previous or impervious and can be selected from among all types of hot-melt adhesives, polyolefins especially polyethylene, polypropylene, amorphous polyolefins, and the like; material containing meltable components comprising fibres or polymeric binders including natural fibres such as cellulose—wood pulp, cotton, jute, hemp; synthetic fibres such as fibreglass, rayon, polyester, polyolefin, acrylic, polyamid, aramid, polytetrafluroethylene metal, polyimide; binders such as bicomponent high melt/low melt polymer, copolymer is polyester, polyvinyl chloride, polyvinyl acetate/chloride copolymer, copolymer polyamide, materials comprising blends wherein some of the constituent materials are not meltable; air and vapour permeable materials including microporous films such as those supplied by EXXON Chemical Co., III, US under the designation EXXAIRE or those supplied by Mitsui Toatsu Co., Japan under the designation ESPOIR NO; and monolithic breathable materials such as HYTRELTM™ available from DuPont and PEBAXTM™ available from ELF Atochem, France.

The waste bag 11 may have any shape or size. Preferred shapes include flat circular type bags, cone shaped bags, truncated cone shaped bags and pyramidal or truncated pyramidal shaped bags and flat T shaped bags. Further, the waste bag 11 may be provided from a unitary piece of material or a number of separate pieces of material which may be identical or different and which may be sealed at their respective peripheries.

In one embodiment, the waste bag 11 may include a wearer facing portion 16 and a garment facing portion 17, which both comprise separate pieces of material. Further, the wearer facing portion 16 and the garment facing portion 17 may each independently comprise more than one section of material. The portions of the waste bag 11 may be secured to each other any known means, including adhesive, thermobonding or pressure bonding.

The waste bag 11 may also contain absorbent material. The absorbent material may comprise any absorbent material which is capable of absorbing and retaining liquids. The absorbent material may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The waste bag 11 is provided with an aperture 21 whereby fecal matter or urine is is received from the body prior to storage within the bag cavity. The aperture 21 is preferably surrounded by a flange 12 and may be provided in any shape or size, such as circular, oblong, heart shaped and may be symmetrical or asymmetrical, preferably the aperture has an oblong configuration either in the longitudinal or in the transversal direction. The flange may comprise projections designed to fit the perineal, genital and/or coccygeal area of the wearer.

The flange 12 should be made of soft, flexible and malleable material to allow easy placement of the flange 12 to the perianal or uro-genital area. Typical materials include nonwoven materials, wovens, open celled thermoplastic foams, closed-cell thermoplastic foams, composites of open celled foams and stretch nonwoven, and films. A closed-cell foam of polyethylene has been found effective, but more preferably an open celled polyure thane foam is used. Preferably, such foams have a thickness within the general range of 0.1 to 5 millimetres and a density of 5 to 250g/m$^2$, more preferably 50 g/m$^2$. Other thermoplastic foam materials, or other suitable plastics sheet materials having the described properties of such foams (i.e., softness, pliability, stretchability, and contractability) might also be used.

The waste bag 11 preferably further comprises an attachment means to secure the device to the wearer. Such means may comprise straps and or a body-compatible pressure sensitive adhesive applied to the wearer facing portion of the waste bag 11 or the flange. Any skin-friendly water resistant pressure sensitive adhesive may be used to attach the device to the perianal or uro-genital area of the wearer, such as hydrocolloid adhesives and hydrogel adhesives. Particularly effective adhesives in providing the desired adhesive properties to secure the flange to the skin of the wearer at the sensitive perianal area, while allowing for relatively painless application and removal, are formed from crosslinking polymers with a plastisicer to form a 3-dimensional matrix. Other preferred adhesives include any of the activatable adhesives described above.

Adhesion Method

Figure 13:
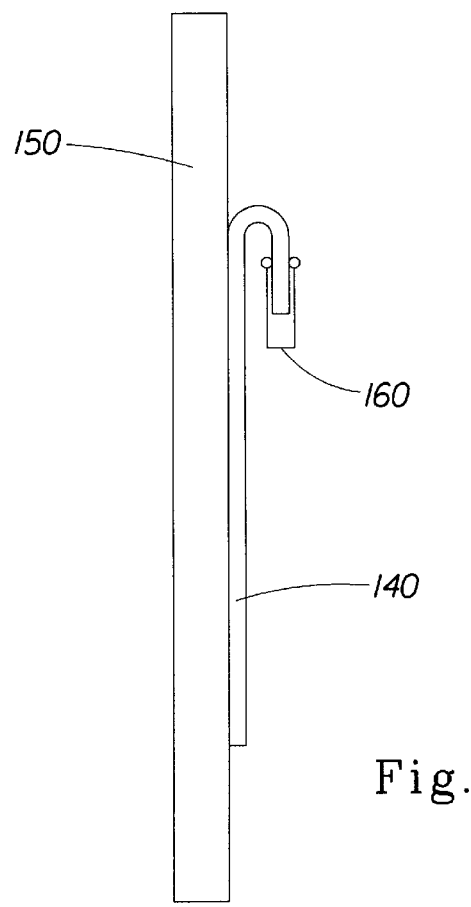
FIG. 13 is a schematic view of a portion of the apparatus used to measure adhesion.

A one-inch wide by 3¼ inch long sample 140 of the adhesive is applied to a smooth stainless steel plate 150 along 3 inches of its length, leaving a ¼ inch "lip" 155 free to pull in the adhesion test. A pressure of 3.3 psi is applied to the adhesive in the 3 inch long region in which it is adhered to the stainless steel plate (i.e., not in the "lip" region) for a duration of one minute. The stainless steel plate 150 should be held at the temperature at which the measurement for adhesion is being sought. (e.g. if one is trying to determine the adhesion value of a particular adhesive at 23 degrees Celsius, the plate should be held at a temperature of 23 degrees Celsius.). The "lip" is grasped in a clamp 160 attached to a Stevens-Farnell QTS-25 Texture Analyzer, model 7113-5kg (available from Leonard Farnell Co. of Hatfield, England). The sample 140 is pulled by the Texture Analyzer at a 180° angle (as shown in FIG. 13) at a constant rate of 10 inches per minute. The adhesion value for the sample is the average resistance to the peel motion recorded by the Texture Analyzer over the length of the sample.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. An absorbent article comprising:
   a topsheet including at least one aperture for receiving fecal waste,
   a backsheet joined with at least a portion of the topsheet,
   an absorbent core disposed between at least a portion of the topsheet and the backsheet; and
   a water-activatable topical adhesive disposed about at least a portion of the at least one aperture for adhering at least a portion of the topsheet to a wearer's skin during use, wherein the water-activatable topical adhesive is substantially anhydrous prior to activation.

2. The absorbent article of claim 1 wherein the water-activatable topical adhesive is activated by the water comprised in one or more of the following: sweat, urine, transepidermal water, humidity, and residual water on the skin from a wipe or bath.

3. The absorbent article of claim 1 wherein the water-activatable topical adhesive is activated by water contained in the absorbent article.

4. The absorbent article of claim 1 wherein the water-activatable topical adhesive includes a material selected from the following group: denture adhesives, denture adhesive laminates, and water-swellable binders.

5. The absorbent article of claim 1 wherein the water-activatable topical adhesive has a pre-activation adhesion value and an activated adhesion value, the activated adhesion value being greater than the pre-activation adhesion value.

6. The absorbent article of claim 5 wherein the pre-aclivation adhesion value is less than about 10 g/in.

7. The absorbent article of claim 5 wherein the activated adhesion value is between about 20 g/in and about 700 g/in.

8. An absorbent article having a first waist region, a second waist region and a crotch region located between the first waist region and the second waist region, the absorbent article comprising:
   a topsheet,
   a backsheet joined with at least a portion of the topsheet,
   an absorbent core disposed between at least a portion of the topshect and the backsheet; and
   a water-activatable adhesive disposed on at least a portion of the article, for the adhering of a wearer contacting surface of the article to a wearer's skin, wherein the water-activatable adhesive has a pre-activation adhesion value and an activated adhesion value, the activated adhesion value being greater than the pre-activation adhesion value, the article further comprising at least one leg cuff extending through at least a portion of the crotch region, wherein the water-activatable adhesive is disposed on the leg cuff.

* * * * *